United States Patent [19]

Kirby

[11] 4,082,774

[45] Apr. 4, 1978

[54] METHYLENEDIOXYBENZENE -- IMPROVED METHOD OF PREPARATION

[75] Inventor: John A. Kirby, Indianapolis, Ind.

[73] Assignee: Eli Lilly and Company, Indianapolis, Ind.

[21] Appl. No.: 487,490

[22] Filed: Jul. 11, 1974

[51] Int. Cl.$^2$ ............................................. C07D 317/50
[52] U.S. Cl. ............................................... 260/340.5 R
[58] Field of Search ....................................... 260/340.5

[56] References Cited

U.S. PATENT DOCUMENTS 3,436,403  4/1969  Cornforth .................... 260/340.5 X Primary Examiner—Richard L. Raymond
Attorney, Agent, or Firm—Steven R. Lammert; Walter E. Butting; Everet F. Smith

[57] ABSTRACT

Methylenation of catechol by reaction with a methylene dihalide under alkaline conditions is improved by adding the pre-formed catechol dianion in a heated protic alkaline medium to a solution of methylene dihalide in dimethyl sulfoxide.

9 Claims, No Drawings

METHYLENEDIOXYBENZENE -- IMPROVED METHOD OF PREPARATION

BACKGROUND OF THE INVENTION

This invention relates to an improved method for preparing methylenedioxybenzene, a compound having the formula

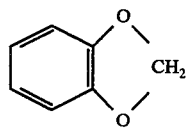

Methylenedioxybenzene and derivatives thereof are valuable intermediates for the preparation of compounds useful in agricultural, pharmaceutical, and veterinary fields. Methylenedioxybenzene has been especially useful in the preparation of synergists for pyrethrin insecticides. It has also been employed in the preparation of 2'-nitro-4',5'-methylenedioxyacetophenone, the starting material for the preparation of the novel antimicrobial 1-lower alkyl or alkylene substituted-6,7-methylenedioxy-4(1H)-oxocinnoline-3-carboxylic acids described in U.S. Pat. No. 3,669,965. The need for methylenedioxybenzene, augmented by the discovery of new commercial uses for the compound and its derivatives, has precipitated a search for a preparative process therefor which is more amenable to its commercial production than are the presently known processes.

Several methods have been disclosed for the preparation of methylenedioxybenzene via the reaction of catechol and a methylene dihalide under alkaline conditions. One such preparation comprises heating a mixture of catechol and a methylene dihalide in aqueous alcoholic alkali. This reaction proceeds very slowly, especially where methylene chloride is the methylenating agent, and prolonged heating under pressure is ordinarily required. An improved method for the preparation of methylenedioxybenzene from catechol and a methylene dihalide was described in U.S. Pat. No. 3,436,403 [see also W. Bonthrone and J. W. Cornforth, *J. Chem. Soc.* (C), 1202 (1969) and references therein] wherein it was disclosed that optimum yields for methylenedioxybenzene were obtained by carrying out the reaction in a highly polar aprotic liquid solvent medium while maintaining a high dilution of the dianions derived from the catechol. The process disclosed in U.S. Pat. No. 3,436,403 was reportedly preferably carried out by adding solid catechol and powdered alkali metal hydroxide separately, simultaneously and slowly, to a solution of methylene dichloride in a highly polar aprotic solvent. It was emphasized that the water liberated in the formation of the dianion by sodium hydroxide is an undesirable by-product, and that it is often preferable to use a base which does not produce such deleterious by-products.

A procedure, such as described in the aforementioned patent, employing simultaneous addition of two solid reactants, although easily carried out on a laboratory scale, is not so practicable on the large scale necessary for the commercial production of methylenedioxybenzene. Solutions of reagents are much more easily handled in large scale plant operations than are the solid reagents themselves. Thus a process for the preparation of methylenedioxybenzene circumventing the handling of solid reagents while still providing good yields would be advantageous.

It is an object of this invention to provide an improved method for the commercial production of methylenedioxybenzene, the improvement being realized not only in the ease of handling of the reagents but also in the yields of methylenedioxybenzene produced. It is another more specific object of this invention to provide an improved, high yielding method for the large scale preparation of methylenedioxybenzene, wherein the catechol derived dianion, in solution, is reacted with a methylene dihalide under protic alkaline conditions.

SUMMARY OF THE INVENTION

This invention comprises an improvement in the method of preparation of methylenedioxybenzene by heating the dianion of catechol and a methylene dihalide under alkaline conditions, said improvement comprising conducting said reaction under protic alkaline conditions by adding the catechol derived dianion in a heated medium comprising one volume of water and about one to ten volumes of dimethyl sulfoxide to a heated solution of methylene dihalide in dimethyl sulfoxide.

DETAILED DESCRIPTION OF THE INVENTION

In the preparation of methylenedioxybenzene by heating catechol and a methylene dihalide under alkaline conditions in a highly polar aprotic solvent, the species which actually reacts with the methylene dihalide to provide the cyclic product is the dianion derivative of the catechol. The improvement provided by this invention comprises the preparation of a solution of this dianion by the reaction of catechol and a suitable base in a mixture of dimethyl sulfoxide and water and the slow addition of the heated dianion solution to a heated solution of a methylene dihalide in dimethyl sulfoxide.

The dianion solution is generally prepared by heating catechol, in solution in dimethyl sulfoxide, with a 5 to 50 percent molar excess of base (with regard to catechol reagent, being mindful that 2 molar equivalents of base are required to convert 1 mole of catechol to its dianion derivative) in the presence of a volume of water sufficient, when mixed with the dimethyl sulfoxide solvent, to provide a protic medium in which the dianion product is soluble.

Suitable bases for the dianion preparation include alkali metal hydroxides and alkali metal carbonates. Exemplary of such bases are sodium hydroxide, potassium hydroxide, sodium carbonate and potassium carbonate. Sodium hydroxide is preferred.

The volume of dimethyl sulfoxide employed in the preparation of the dianion solution is generally determined by the weight of the catechol starting material; usually from about 100 to 300 ml. of dimethyl sulfoxide is used for each mole of catechol reagent. Because of dianion solubility characteristics and economic considerations, it is preferred that about 200 ml. of dimethyl sulfoxide be employed for each mole of catechol reagent.

As stated hereinbefore, the solvent for the dianion preparation comprises dimethyl sulfoxide and water. The incorporation of from about 25 to about 200 ml. of water per mole of catechol reagent in the medium for the dianion preparation provides a suitable solvent mixture. Preferably the medium for the dianion solution comprises about 200 ml. of dimethyl sulfoxide and about 80 to 100 ml. of water for each mole of catechol starting material.

Generally the medium for the dianion solution comprises one volume of water and about 1 to 10 volumes of dimethyl sulfoxide. Under the preferred conditions, however, the dianion medium comprises about 1.0 to about 3.0 volumes of dimethyl sulfoxide for every volume of water therein.

In practice the dianion solution is preferably prepared by adding an aqueous solution of sodium hydroxide (the concentration of the sodium hydroxide therein being such that the required amount of base for the dianion preparation is dissolved in the preferred volume of water) to a heated solution of the catechol in dimethyl sulfoxide. Thus on a 10 mole scale, for example, the dianion solution can be prepared by adding a solution of about 850 g. of sodium hydroxide in about 900 ml. of water to a heated solution of 1.1 kg. of catechol in about 2 liters of dimethyl sulfoxide. For the sake of convenience, a 50 percent (w/w) aqueous sodium hydroxide is generally employed in the dianion preparation.

In order to effect completion of the dianion formation and to maintain the dianion thus prepared in solution, the mixture of catechol and base in the protic medium is preferably heated to 80° to 100° C. for about 15 to 30 minutes before, and also during, the time said solution is slowly added to a heated solution of a methylene dihalide in dimethyl sulfoxide.

The methylene dihalide solution to which the dianion solution is added, is prepared by mixing about 1.1 molar equivalents (relative to the catechol) of a suitable methylene dihalide reagent with a volume of dimethyl sulfoxide, which volume of dimethyl sulfoxide under preferred conditions, is equivalent to from about one to three times the volume of dimethyl sulfoxide employed in preparing the dianion solution. Alternatively, the suitable volume of dimethyl sulfoxide to be employed in preparation of the methylene dihalide solution can be determined directly in terms of the scale of the reaction. Thus, the volume of dimethyl sulfoxide employed in the preparation of the methylene dihalide solution is, preferably, such that in the final reaction mixture (after dianion solution added) the weight ratio of dimethyl sulfoxide to initial dianion reactant is at least 2.5/1. It is preferable to prepare the methylene dihalide solution by using dimethyl sulfoxide as the solvent for 1.1 to 2.0 molar equivalents (per amount of catechol reagent) of a suitable methylene dihalide.

Exemplary of suitable methylene dihalides are methylene dichloride, methylene dibromide, methylene diiodide, and methylene chlorobromide. Methylene dichloride is preferred.

The reaction of the dianion with the methylene dihalide is carried out preferably by adding the solution of the dianion in a heated (80°–100° C.) protic medium dropwise to a refluxing solution of the methylene dihalide in dimethyl sulfoxide.

The temperature of the refluxing reaction mixture varies during the course of the reaction. As the methylene dihalide is consumed the temperature of the refluxing mixture increases. Under preferred conditions, the temperature of the refluxing reaction mixture will usually vary from about 90° to about 140°, the highest temperature being attained after the addition of the dianion solution has been completed.

Following the addition of the dianion solution the temperature of the protic reaction medium is preferably maintained at about 100° to 140° for about 1 to 2 hours to insure completion of the reaction.

The product methylenedioxybenzene is isolated from the reaction mixture by standard procedures, such comprising distillation of excess methylene dihalide and subsequent steam distillation of the product.

Yields of methylenedioxybenzene obtained by the improved process of this invention, even on large scale (10 moles and up) preparations, are consistently above 80 percent, with some yields ranging up to 95 percent and above.

The following examples are provided to further illustrate this invention. It is not intended that this invention be limited in scope by reason of any of these examples.

EXAMPLE

Preparation of methylenedioxybenzene

A. A solution of 11 g. of catechol, 16 g. of 50 percent aqueous sodium hydroxide and 75 ml. of dimethyl sulfoxide (DMSO) was heated to about 90° C. and was subsequently added over a 10 minute period to a refluxing mixture of 100 ml. of DMSO and 20 ml. of methylene dichloride. The reaction mixture was heated for 45 minutes, and thereafter the excess methylene dichloride was distilled from the mixture. About 50 ml. of water was added to the mixture and the product methylenedioxybenzene was steam distilled, additional water being added to the mixture at about the same rate as that of distillation. The distillate was extracted with diethyl ether. The ether extract was concentrated in vacuo to provide 10.4 g. (87 percent) of methylenedioxybenzene as a colorless oil.

B. A solution of 110 g. of catechol, 160 g. of 50 percent aqueous sodium hydroxide, and 100 ml. of DMSO was stirred and heated to 95°–100° C. for 15 minutes. The temperature of the solution was maintained in the same range while the solution was added over a period of 30 minutes to a refluxing solution of 100 ml. of methylene dichloride in 400 ml. of DMSO. After the addition, the temperature of the refluxing reaction mixture reached 120° C., and was maintained at this level for 2.5 hours. Following the same isolation procedures as indicated in (A) above, 99.7 g. (80 percent) of methylenedioxybenzene was isolated.

C. Following the same procedure as in (B), except that the dianion solution was added during 20 minutes and only a one hour reaction time was provided after the addition, 100 g. (82 percent) of methylenedioxybenzene was isolated.

D. A solution of 110 g. of catechol, 120 ml. of 50 percent aqueous sodium hydroxide and 200 ml. of DMSO was heated to 98° C. and stirred at that temperature for 30 minutes. This solution at 98° C. was added over a 30 minute period to a refluxing solution of 120 ml. of methylene dichloride in 300 ml. of DMSO. Thereafter, the reaction mixture was stirred at reflux for 1.5 hours. Steam was then passed into the mixture to achieve steam distillation of the product. The distillate (600 ml.) was extracted with 100 ml. of methylene dichloride, which extract was washed once with 50 ml. of deionized water. The methylene dichloride solution was then concentrated in vacuo at 40° C. to yield 119.4 g. of a colorless oil. Gas chromatographic analysis showed 97.5 percent methylenedioxybenzene. Corrected yield—116.4 g. (95.4 percent).

E. A 40 l. portable, stainless steel pot was charged with 14.0 l. of DMSO and 7.7 kg. of catechol. To this mixture at 90° C. was added 8.4 l. of 50 percent (w/w) aqueous sodium hydroxide. The resulting solution of dianion was heated to 105° C. and then added over a 1 hour period to a refluxing solution of 21 l. of DMSO and 7 l. of methylene dichloride in a 30 gal. stainless steel still. During the addition the pot temperature rose from 92° to 108° C. The reaction mixture was subsequently stirred at reflux for about 2 hours, during which time the temperature rose from 108° to 120° C. Steam distillation, accomplished by injecting steam into the mixture through a valve at the bottom of the still, yielded 70 l. of distillate in 2 hours. The aqueous distillate was extracted with 7 l. of methylene dichloride. The methylene dichloride solution was separated and washed with 7 l. of deionized water. Analysis of the methylene dichloride solution (16.9 kg.) by vapor phase chromatography showed it to be 41.7 percent methylenedioxybenzene and 58.3 percent methylene dichloride. Corrected yield of methylenedioxybenzene—7.05 kg. (82.5 percent).

I claim:

1. In the process wherein the dianion of catechol is reacted with a methylene dihalide under alkaline conditions to form methylenedioxybenzene, the improvement which comprises conducting said reaction under protic alkaline conditions by adding the dianion in a heated medium comprising one volume of water and about 1 to 10 volumes of dimethyl sulfoxide to a heated solution of a methylene dihalide in dimethyl sulfoxide.

2. The improvement according to claim 1 wherein the methylene dihalide is methylene dichloride.

3. The improvement according to claim 2 wherein the medium for the dianion comprises about 1 to about 3 volumes of dimethyl sulfoxide and 1 volume of water.

4. The improvement according to claim 3 wherein aqueous sodium hydroxide is employed in the preparation of the dianion solution.

5. The improvement according to claim 3 wherein the dianion medium comprises about 200 ml. of dimethyl sulfoxide for each mole of catechol dianion.

6. The improvement according to claim 5 wherein a heated solution of the catechol dianion is added to a refluxing solution of about 1.1 molar equivalents of methylene dichloride in dimethyl sulfoxide.

7. The improvement according to claim 6 wherein the colume of dimethyl sulfoxide in the methylene dichloride solution is from about one to about three times the volume of dimethyl sulfoxide in the dianion solution.

8. The improvement according to claim 7 wherein the dianion solution is heated to 80°–100° C. and is added dropwise to a refluxing solution of 1.1 to 2.0 molar equivalents of methylene dichloride in dimethyl sulfoxide.

9. The improvement according to claim 8 wherein in the reaction mixture the weight ratio of dimethyl sulfoxide to dianion reactant is at least 2.5/1.

* * * * *